US006179831B1

(12) United States Patent
Bliweis (10) Patent No.: US 6,179,831 B1
(45) Date of Patent: Jan. 30, 2001

(54) METHOD OF CRYOABLATING BENIGN PROSTATE HYPERPLASIA (75) Inventor: Mordechai Bliweis, Haifa (IL)

(73) Assignee: Galil Medical Ltd., Yokneam (IL)

(*) Notice: Under 35 U.S.C. 154(b), the term of this patent shall be extended for 0 days.

(21) Appl. No.: 09/301,576

(22) Filed: Apr. 29, 1999

(51) Int. Cl.[7] .................................................. A61B 18/18
(52) U.S. Cl. .................................. 606/21; 606/24
(58) Field of Search ........................................ 606/20–28

(56) References Cited

U.S. PATENT DOCUMENTS

| 5,522,870 | 6/1996 | Ben-Zion . | |
|---|---|---|---|
| 5,531,676 | * 7/1996 | Edwards et al. | 604/22 |
| 5,540,062 | 7/1996 | Maytal . | |
| 5,741,248 | * 4/1998 | Stern et al. | 606/21 |
| 6,102,886 | * 8/2000 | Lundquist et al. | 604/22 |
| 6,106,517 | * 8/2000 | Zupkas | 606/20 |

* cited by examiner

Primary Examiner—Linda C. M. Dvorak
Assistant Examiner—David M. Ruddy
(74) Attorney, Agent, or Firm—Mark M. Friedman (57) ABSTRACT

A method for treating benign prostate hyperplasia is provided. The method is effected by (a) inserting a cystoscope into a prostatic urethra portion of a urethra of a patient having benign prostate hyperplasia; (b) guiding a probe of a cryoprobe having an operating tip through a channel of the cystoscope to an portion of the prostatic urethra; (c) navigating the operating tip through a wall of the prostatic urethra into at least one location at a time of a prostate of the patient; and (d) operating the cryoprobe thereby cooling the operating tip and producing an ice-ball of prostate tissue around the operating tip, so as to locally freeze a portion of the prostate, yet substantially avoid freezing the prostatic urethra.

27 Claims, 8 Drawing Sheets

METHOD OF CRYOABLATING BENIGN PROSTATE HYPERPLASIA

FIELD AND BACKGROUND OF THE INVENTION

The present invention relates to a method for treating benign prostate hyperplasia (BPH) and, more particularly, to a method devised for cryoablating BPH through the urethra, yet minimizing the damage inflicted upon urethral tissue in course of treatment.

BPH, which affects a large number of adult men, is a non-cancerous enlargement of the prostate. BPH frequently results in a gradual squeezing of the portion of the urethra which traverses the prostate, also known as the prostatic urethra. This causes patients to experience a frequent urge to urinate because of incomplete emptying of the bladder and a burning sensation or similar discomfort during urination. The obstruction of urinary flow can also lead to a general lack of control over urination, including difficulty initiating urination when desired, as well as difficulty in preventing urinary flow because of the residual volume of urine in the bladder, a condition known as urinary incontinence. Left untreated, the obstruction caused by BPH can lead to acute urinary retention (complete inability to urinate), serious urinary tract infections and permanent bladder and kidney damage.

Most males will eventually suffer from BPH. The incidence of BPH for men in their fifties is approximately 50% and rises to approximately 80% by the age of 80. The general aging of the United States population, as well as increasing life expectancies, is anticipated to contribute to the continued growth in the number of BPH sufferers.

Patients diagnosed with BPH generally have several options for treatment: watchful waiting, drug therapy, surgical intervention, including transurethral resection of the prostate (TURP), laser assisted prostatectomy and new less invasive thermal therapies.

Currently, of the patients suffering from BPH, the number of patients who are actually treated by surgical approaches is approximately 2% to 3%. Treatment is generally reserved for patients with intolerable symptoms or those with significant potential symptoms if treatment is withheld. A large number of the BPH patients delay discussing their symptoms or elect "watchful waiting" to see if the condition remains tolerable.

The development of a less invasive treatment for BPH could result in a substantial increase in the number of BPH patients who elect to receive interventional therapy.

Drug Therapies:

Some drugs are designed to shrink the prostate by inhibiting or slowing the growth of prostate cells. Other drugs are designed to relax the muscles in the prostate and bladder neck to relieve urethral obstruction. Current drug therapy generally requires daily administration for the duration of the patient's life.

Surgical Interventions:

The most common surgical procedure, transurethral resection of the prostate (TURP), involves the removal of the prostate's core in order to reduce pressure on the urethra. TURP is performed by introducing an electrosurgical cutting loop through a cystoscope into the urethra and "chipping out" both the prostatic urethra and surrounding prostate tissue up to the surgical capsule, thereby completely clearing the obstruction. It will be appreciated that this procedure results in a substantial damage inflicted upon the prostatic urethra.

Laser Ablation of the Prostate:

Laser assisted prostatectomy includes two similar procedures, visual laser ablation of the prostate (V-LAP) and contact laser ablation of the prostate (C-LAP), in which a laser fiber catheter is guided through a cystoscope and used to ablate and coagulate the prostatic urethra and prostatic tissue. Typically, the procedure is performed in the hospital under either general or spinal auesthesia, and an overnight hospital stay is required. In V-LAP, the burnt prostatic tissue then necroses, or dies and over four to twelve weeks is sloughed off during urination. In C-LAP, the prostatic and urethral tissue is burned on contact and vaporized. Again, it will be appreciated that these procedures result in a substantial damage inflicted upon the prostatic urethra.

Heat Ablation Therapies:

Other technologies under development or practice are non-surgical, catheter based therapies that use thermal energy to preferentially heat diseased areas of the prostate to a temperature sufficient to cause cell death. Thermal energy forms being utilized include microwave, radio frequency (RF) and high frequency ultrasound energy (HIFU). Both microwave and RF therapy systems are currently being marketed worldwide. Heat ablation techniques, however, burn the tissue, causing irreversible damage to peripheral tissue due to protein denaturation, and destruction of nerves and blood vessels. Furthermore, heat generation causes secretion of substances from the tissue which may endanger the surrounding area.

Transurethral RF Therapy:

Transurethral needle ablation (TUNA) heats and destroys enlarged prostate tissue by sending radio waves through needles urethrally positioned in the prostate gland. The procedures prolongs about 35 to 45 minutes and may be performed as an outpatient procedure. However TUNA is less effective than traditional surgery in reducing symptoms and improving urine flow. TUNA also burn the tissue, causing irreversible damage to peripheral tissue due to protein denaturation, and destruction of nerves and blood vessels. Furthermore, as already discussed above, heat generation causes secretion of substances from the tissue which may endanger the surrounding area.

Cryoablation Therapy:

During conventional cryoablation therapy part of the prostate gland is frozen by pencil like probe placed into the gland through the perineum, an ultrasound is used throughout the procedure to monitor the progress of the freezing. The limitations of this procedure are its invasiveness.

There is thus a widely recognized need for, and it would be highly advantageous to have, a method for cryoablating BPH through the urethra, yet minimizing the damage inflicted upon urethral tissue in course of treatment and which is devoid of the above limitations associated with prior art techniques.

SUMMARY OF THE INVENTION

According to the present invention there is provided a method for treating benign prostate hyperplasia, the method comprising the steps of (a) inserting a cystoscope into a prostatic urethra portion of a urethra of a patient having benign prostate hyperplasia; (b) guiding a cryoprobe having an operating tip through a channel of the cystoscope to a portion of the prostatic urethra; (c) navigating the operating tip through a wall of the prostatic urethra into at least one location at a time of a prostate of the patient; and (d) operating the cryoprobe thereby cooling the operating tip and producing an ice-ball of prostate tissue around the operating tip, so as to locally freeze a portion of the prostate, yet substantially avoid freezing the prostatic urethra.

According to further features in preferred embodiments of the invention described below, the method further comprising the step of retracting the cryoprobe from the channel of the cystoscope.

According to still further features in the described preferred embodiments the method further comprising the step of retracting the cystoscope from the urethra.

According to still further features in the described preferred embodiments the step of inserting the cystoscope into the prostatic urethra portion of the urethra of the patient having benign prostate hyperplasia is aided using an optical probe inserted through an optical channel of the cystoscope.

According to still further features in the described preferred embodiments the step of navigating the operating tip through the wall of the prostatic urethra into at least one location at a time of the prostate of the patient is aided using an optical probe inserted through an additional channel of the cystoscope.

According to still further features in the described preferred embodiments the step of navigating the operating tip through the wall of the prostatic urethra into at least one location at a time of the prostate of the patient is aided using a built-in optical channel of the cystoscope.

According to still further features in the described preferred embodiments the step of navigating the operating tip through the wall of the prostatic urethra into at least one location at a time of the prostate of the patient is aided using ultrasound monitoring.

According to still further features in the described preferred embodiments the step of navigating the operating tip through the wall of the prostatic urethra into at least one location at a time of the prostate of the patient is aided using an optical channel of the cystoscope and ultrasound monitoring.

According to still further features in the described preferred embodiments the method further comprising the step of prior to executing the step of inserting the cystoscope into the prostatic urethra portion of the urethra of the patient having benign prostate hyperplasia, providing the patient with local anesthesia.

According to still further features in the described preferred embodiments the method further comprising the step of heating the operating tip so as to melt at least an inner portion of the ice ball and navigating the operative away from the portion of the prostate.

According to still further features in the described preferred embodiments the cystoscope has a navigation mechanism operative therewith, the navigation mechanism serves to effect the step of navigating the operating tip through the wall of the prostatic urethra into at least one location at a time of the prostate of the patient.

According to still further features in the described preferred embodiments the operating tip of the cryoprobe is formed with a sharp end so as to minimize the wound formed in the wall of the prostatic urethra when effecting the step of navigating the operating tip through the wall of the prostatic urethra into at least one location at a time of the prostate of the patient.

According to still further features in the described preferred embodiments the cryoprobe is flexible at least at a portion thereof adjacent the operating tip.

According to still further features in the described preferred embodiments said probe of said cryoprobe includes a heat exchanger coupled to an orifice, the orifice opening into a jacket; said jacket forming a reservoir capable of housing a fluid in contact with said at least one location, at a time, of said prostate of said patient; said cryoprobe further includes two gas sources providing two gases, each of said two gas sources being independently connected to said heat exchanger of said probe, and a mechanism for allowing and stopping a flow of each of said two gases through said orifice.

According to still further features in the described preferred embodiments said gas sources are pressurized, pressurized gas sources are gas reservoirs containing gas under pressure.

According to still further features in the described preferred embodiments said gas sources include one or more compressors, which draw gas from a reservoir containing gas at a lower pressure than desired.

According to still further features in the described preferred embodiments the heat exchanger is a thin tube or a porous matrix heat exchanger.

According to still further features in the described preferred embodiments the probe of the cryoprobe includes (i) a heat exchanger coupled to an orifice, the orifice opening into a jacket; and (ii) the jacket which is in contact with the surface to be heated and cooled, the jacket forming a reservoir capable of housing a fluid in contact with a surface to be heated and cooled; the cryoprobe further includes (a) two independent connections for pressurized gas sources, connected to the heat exchanger; (b) temperature generation mechanism, coupled to the probe, including (i) two independent pressurized gas sources, connected to the probe through the two independent connections; (ii) controllable gas flow valves to permit or preclude a flow of each of gases from the independent pressurized gas sources into the probe; and (c) processing mechanism for controlling the controllable gas flow rate valves according to predetermined operating conditions.

According to still further features in the described preferred embodiments the cryoprobe further includes a data input mechanism, to provide operation data to the processing mechanism.

According to still further features in the described preferred embodiments the data input mechanism includes a keyboard.

According to still further features in the described preferred embodiments the cryoprobe further includes display mechanism to display data written to, or read from, the processing mechanism.

According to still further features in the described preferred embodiments the data input mechanism includes a communication port.

According to still further features in the described preferred embodiments the communication port is an RS232 port.

According to still further features in the described preferred embodiments the data input mechanism includes a magnetic or optical reading mechanism, to read pre-prepared data.

According to still further features in the described preferred embodiments the cryoprobe further includes a temperature-reading mechanism located at or near the operating tip, which temperature-reading mechanism provides temperature readings to the processing mechanism.

According to still further features in the described preferred embodiments the temperature-reading mechanism includes one or more thermocouples.

According to still further features in the described preferred embodiments the cryoprobe further includes a pressure-reading mechanism located between the pressurized gas source and the probe, to provide to the processing mechanism readings corresponding to pressure supplied by each of the pressurized gas sources.

According to still further features in the described preferred embodiments at least a portion of the cryoprobe is substantially flexible.

According to still further features in the described preferred embodiments at least a portion of the cryoprobe is substantially rigid.

The present invention successfully addresses the shortcomings of the presently known configurations by providing a method devised for cryoablating BPH through the urethra, yet minimizing the damage inflicted upon urethral tissue in course of treatment.

BRIEF DESCRIPTION OF THE DRAWINGS

The invention herein described by way of example only, with reference to the accompanying drawings, wherein.

DESCRIPTION OF THE PREFERRED EMBODIMENTS

The present invention is of a minimally invasive method which can be used for treating benign prostate hyperplasia (BPH). Specifically, the present invention can be used for cryoablating BPH through the urethra, while minimizing the damage inflicted upon urethral tissue in course of treatment.

The principles and operation of a method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1–8 illustrate cryoprobes (i.e., cryosurgery devices) which are described in U.S. Pat. Nos. 5,522,870 and 5,540,062, both are incorporated by reference as if fully set forth herein, and which are used, according to preferred embodiments, to implement the method according to the present invention.

Figure 1:
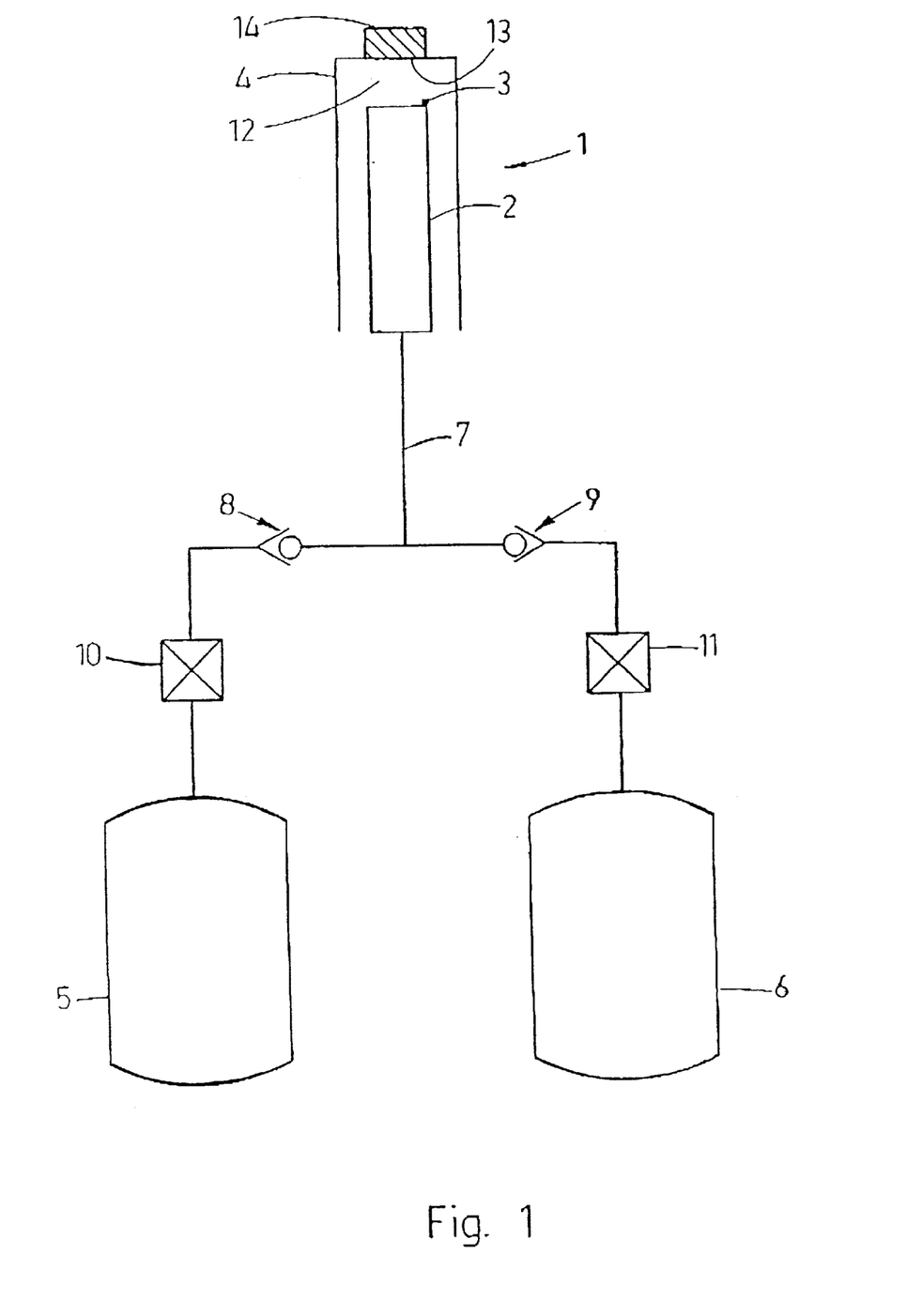
FIG. 1 is a schematic representation of a cryoprobe according to one embodiment of U.S. Pat. No. 5,522,870 which is preferably employed to implement the method of the present invention.

Looking now at FIG. 1, numeral 1 generally indicates a probe, as disclosed in U.S. Pat. No. 5,522,870, comprising a heat-exchanger 2, an orifice 3, and an isolated jacket 4, which together constitute a Joule-Thompson device. Two gas reservoirs, 5 and 6, containing gas under pressure of about 40 MPa are connected to heat-exchanger 2, via line 7, through one-way valves 8 and 9, and on-off valves 10 and 11. Alternatively, two compressors can be provided, to compress the gases of reservoirs 5 and 6.

When an on-off valve (10 or 11) is opened, gas flows through line 7 into heat exchanger 2, and exits orifice 3 to form a cryogen pool, indicated by numeral 12. Probe surface 13 is either cooled or heated by this pool, depending on the gas used at the time, and cools the surface of the object schematically indicated at 14, which is brought into contact with it.

Figure 2:
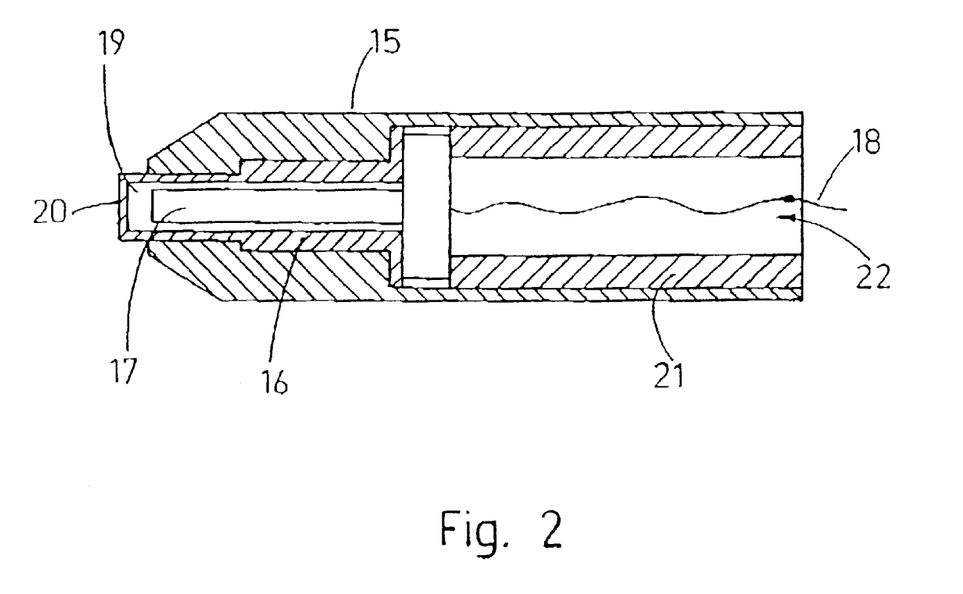
FIG. 2 is a detailed representation of a cryoprobe according to one embodiment of U.S. Pat. No. 5,522,870 which is preferably employed to implement the method of the present invention, shown in cross-section.

The design of a probe, according to one embodiment is more fully illustrated in FIG. 2. An isolating sleeve 15 houses the various parts of the probe, which include a steel encapsulation 16, containing a cryocooler 17. High pressure gas is supplied through a supply line 18, and expands through an orifice (not shown). The hot or cold gas creates a pool 19, which is in contact with the heating/cooling surface 20, which is the surface used to apply cold and heat to the treated body. An additional sleeve 21 is provided for holding the cryocooler 17 in place, and the exhaust gas leaves the probe through the empty space 22 therein.

Figure 3:
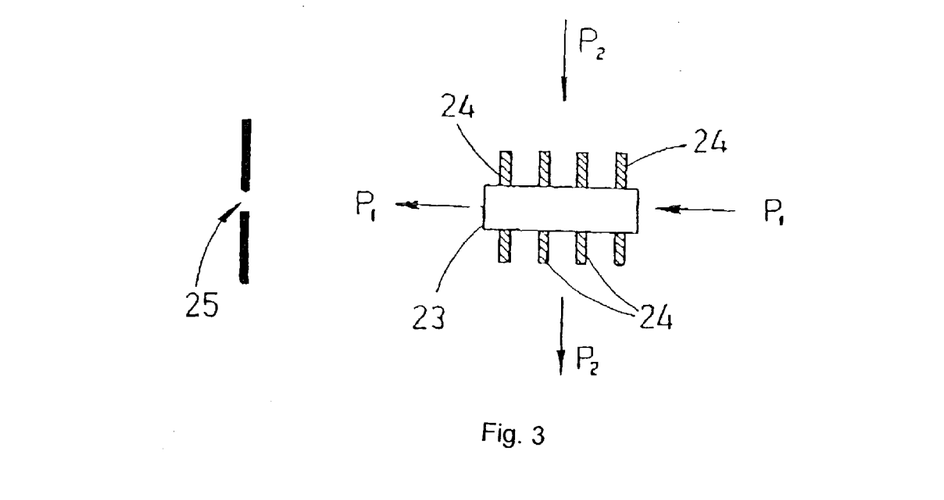
FIG. 3 schematically shows a portion of a finned tube employed with the cryoprobe of FIG. 1.

FIG. 3 schematically shows a segment of a finned tube 23 of a heat exchanger used with the probe. Fins 24 are distributed along tube 23. Gas at a high pressure, P1, flows within tube 23, towards orifice 25, while exhaust gas, at a lower pressure P2, flows across tube 23, as shown by the arrows.

Figure 4:
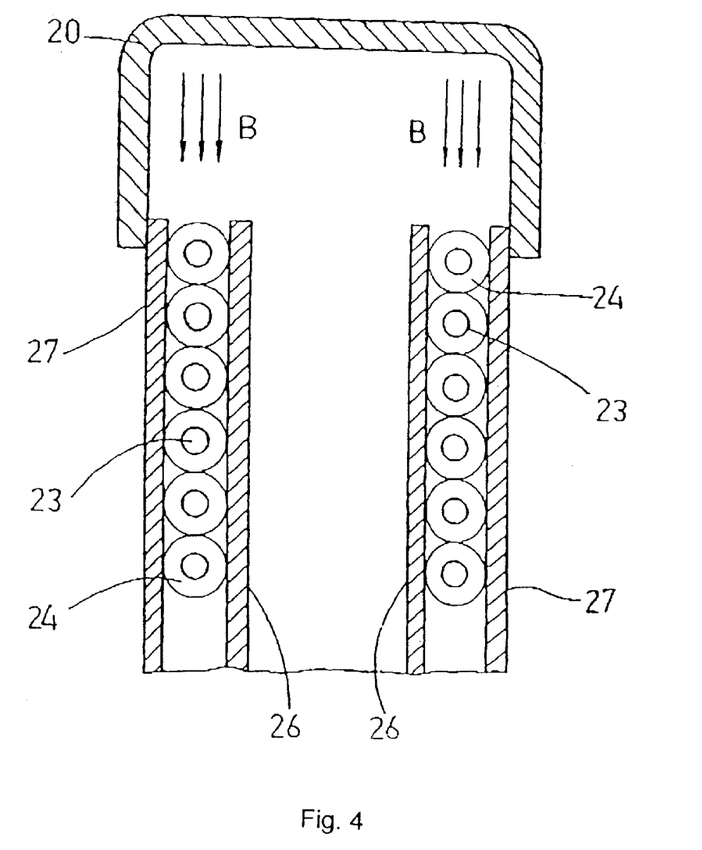
FIG. 4 is a schematic cross section of a cryoprobe according to one embodiment of U.S. Pat. No. 5,522,870, which is preferably employed to implement the method of the present invention, the heat exchanger being shown.
Figure 5:
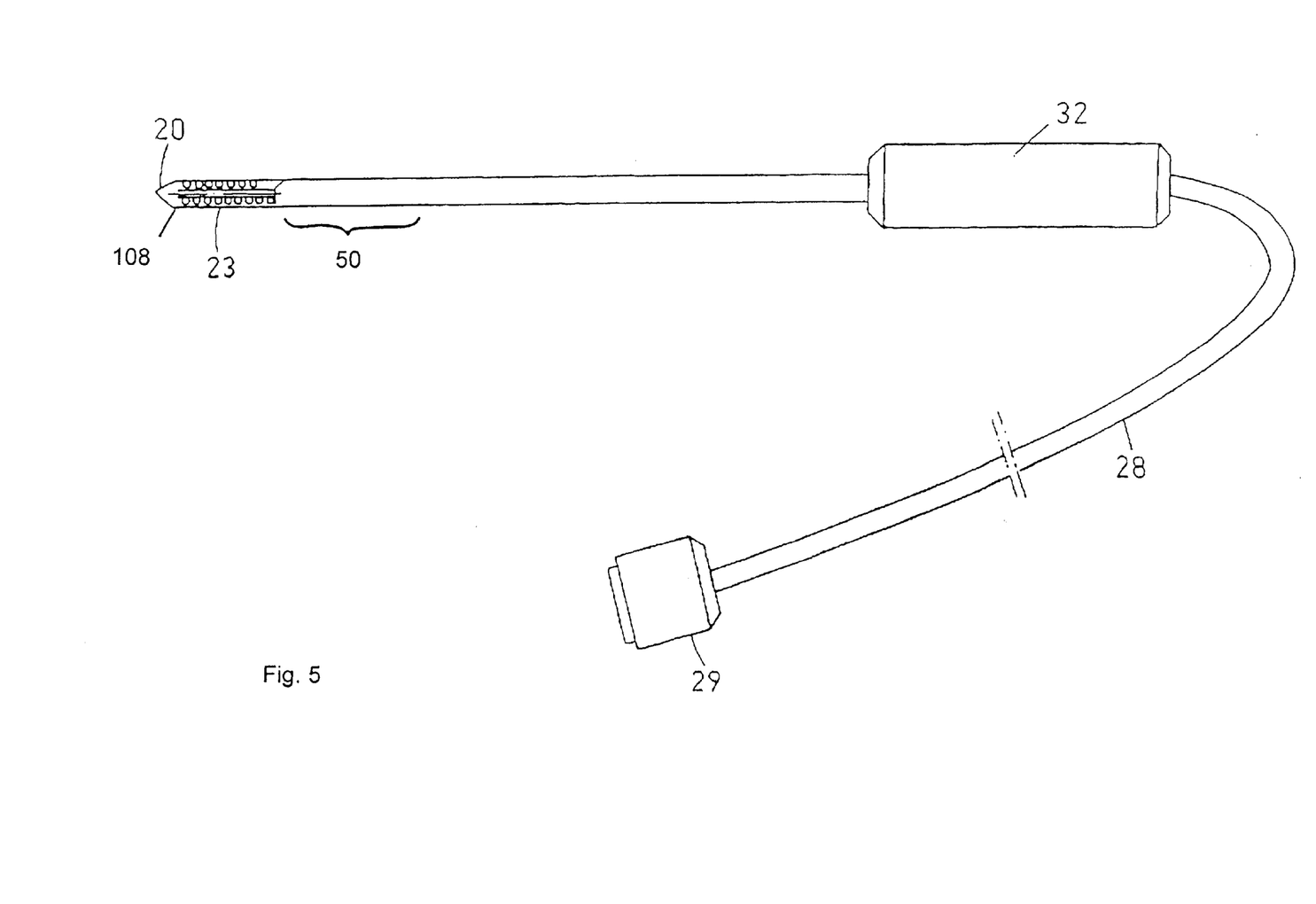
FIG. 5 schematically shows a thin probe according to a preferred embodiment of U.S. Pat. No. 5,522,870, which is preferably employed to implement the method of the present invention.

In FIG. 4 the heat-exchanger is seen to be made of high pressure tubes 23, with fins 24, which are contained within an inner mandrel 26 and an outer mandrel 27. Gas backflowing from the cooled or heated surface 20, indicated by arrows B, flows into the heat-exchanger and comes into contact with the outer surface of finned tube 23, thus exchanging heat with the gas flowing within it.

The probes described above can be made thin enough to function as a urethral probe, because the heating/cooling device can be accommodated even in very small volumes since no space-consuming parts are required.

Figure 8:
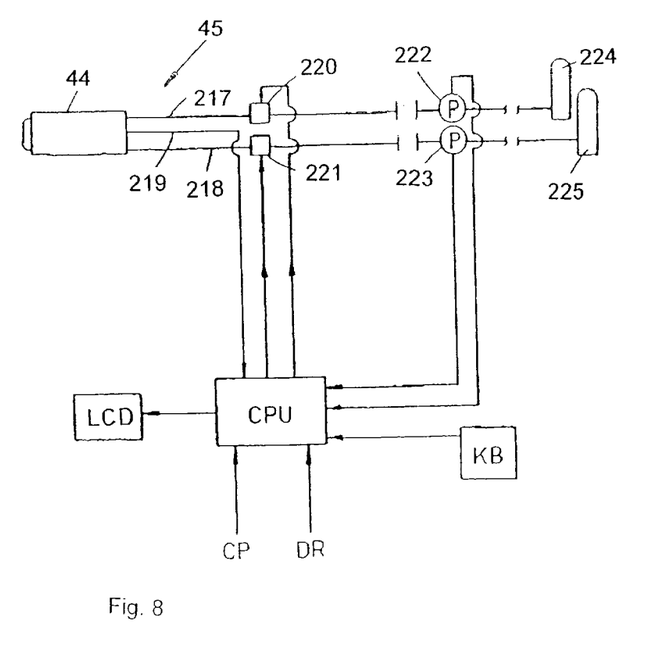
FIG. 8 schematically illustrates the controlled operation of the cryoprobe of FIG. 6.

A thin probe thus designed is shown in FIG. 8, in which contact surface 20 is pointed. Because of the thinness of the probe, the inner and outer mandrels are reduced in thickness, and are not shown for the sake of clarity. The probe holder 32, in this embodiment of the invention, can be located far from the pointed end of the probe.

Figure 6:
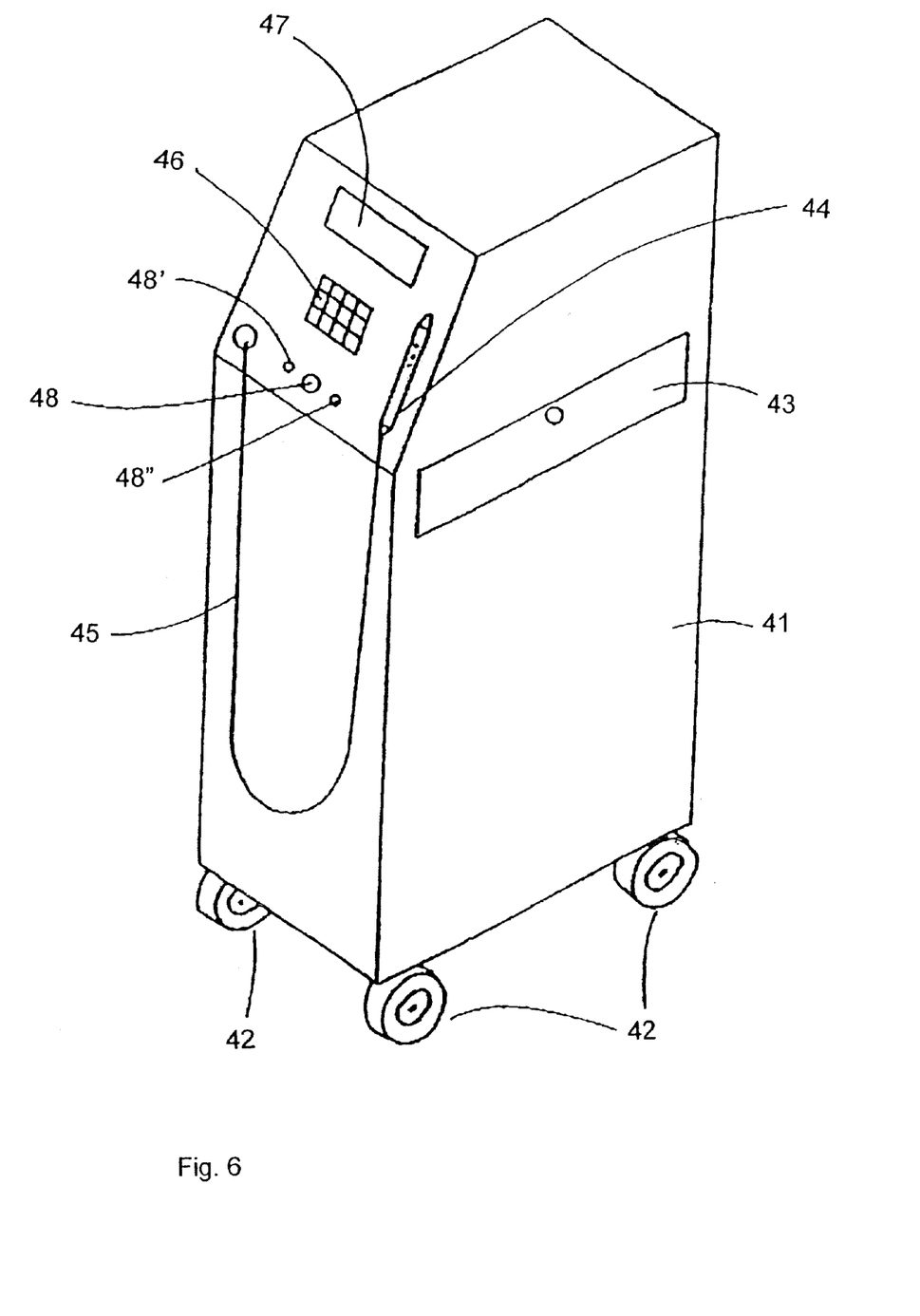
FIG. 6 is a schematic perspective view of a cryoprobe according to one embodiment of U.S. Pat. No. 5,540,062 which is preferably employed to implement the method of the present invention.

FIG. 6 illustrates a device as disclosed in U.S. Pat. No. 5,540,062. This device is designed to be movable and self-supporting, and does not require connection to outside gas sources. It includes of a body 41, provided with wheels 42, which houses two gas reservoirs (not shown). The reservoirs can be replaced through the backdoor, which is not see in the Figure. An additional door 43 gives access to the inside of the body, and is used for parts replacement and maintenance, as well as for housing spare parts.

A probe 44 is connected to the gas reservoirs and to a microprocessor through line 45. All connections are within body 41. A keyboard 46 and a display 47 are provided on the front panel of the device, along with on-off switch 48 control lights 48' and 48", which can be used to indicate the operation status of the device, e.g., to indicate at any given time whether it is cooling or heating.

Since the electric power requirements of the apparatus are relatively very low, the apparatus is powered by a DC source, such as a battery, but may alternatively be connected to an AC source.

Figure 7:
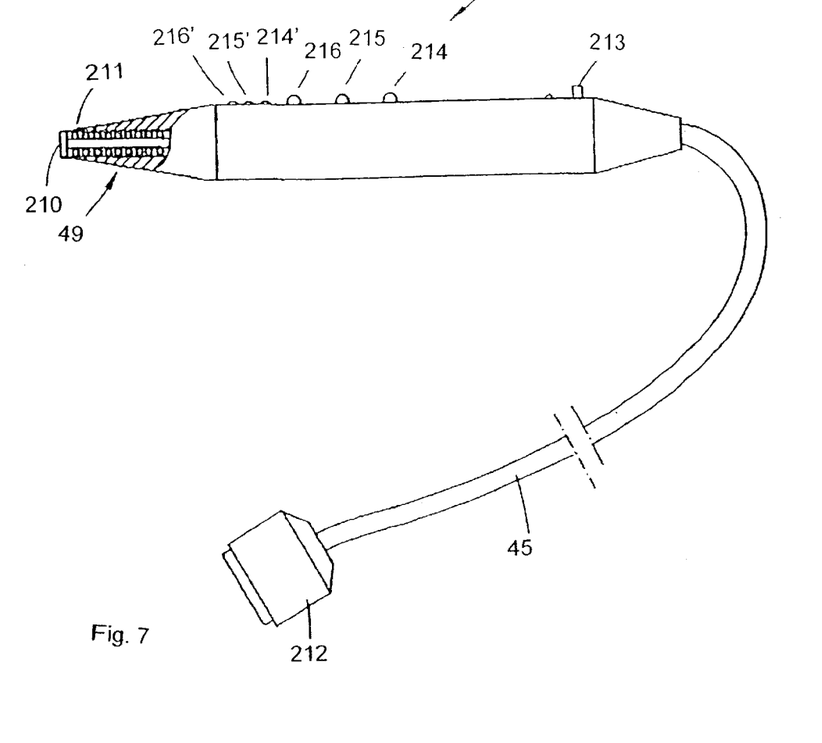
FIG. 7 schematically shows a probe, according to one embodiment of U.S. Pat. No. 5,540,062, which is preferably employed to implement the method of the present invention, shown in partial cross-section.

FIG. 7 shows probe 44 of FIG. 1 in greater detail. The Joule-Thomson heat exchanger 49 serves contact surface 210, which is heated or cooled, depending on the nature of the gas flowing therethrough. Thermocouple 211 is in close contact with the inner part of contact surface 210, and detects the temperature at that location. The thermocouple wire is led to the processing mechanism through line 45 and connector 212, leaving the probe is exhausted to the atmosphere either through connections in the probe, or at connector 212.

The probe is provided with a main switch 213, operating switches 214, 215 and 216, and monitor lights 214', 215' and 216'. These switches operate the probe towards cooling or heating, or for preset cooling/heating cycles, and the lights indicate the operation being performed. Manual operation or microprocessor-controlled operation can be chosen.

Looking now at FIG. 8, a central processing unit (CPU) controls the operation of the device, according to predetermined operating conditions provided thereto. Programming of the operating conditions can be made through keyboard 46 of FIG. 6 (indicated by KB in the Figure), or through a communication port, CP, connected to a programming computer, or through a data reader, DR, e.g., a magnetic or optical reader. The data can be displayed on a display, e.g., a liquid crystal display (LCD), and the keyboard can be used also to read data from the CPU and to display them on the LCD. The CPU can be provided with a substantial memory, so as to store not only operating parameters to be controlled, but also data received during the operation, e.g., temperature or pressure readings.

Data contained in the memory of the CPU can be printed out, e.g., through an RS232 or similar port.

Line 45 of probe 44 contains two incoming gas lines, 217 and 218, as well as an outgoing thermocouple line 219, the readings of which are fed to the CPU. In response, and in order to maintain the preprogrammed temperature in the probe contact surface, the CPU operates the two controllable valves 220 and 221, which control the flow of gas into probe 44. Two pressure gauges, 222 and 223, provide pressure readings to the CPU, which relate to the pressure in reservoirs 224 and 225.

The various portions of the probes described hereinabove may be substantially rigid or substantially flexible. According to a preferred embodiment, and for reasons further elaborated hereinunder, at least a portion 50 (FIG. 5) of the probe, proximally adjacent to its operating tip 108 (FIG. 5) is flexible. The flexible portion is made for example of, fluorocarbon polymer (e.g., TEFLON) or of silicon materials which can withstand the temperatures associated with the operation of the probe.

According to preferred embodiments of the present invention the cooling gas is selected from the group consisting of argon, nitrogen, air, krypton, $CF_4$, xenon, $CO_2$, and $N_2O$ or any mixture of gases. Gases which may be used for heating include helium or any mixture of gases.

The cryoprobes described herein are used according to preferred embodiments of the present invention to implement a method for treating benign prostate hyperplasia. It will, however, be appreciated that other cryoprobes featuring a flexible portion at least proximally adjacent their operative tip can be used as well, examples include, but are not limited to, flexible cryoprobes manufactured by ERBE Elektromedizin Gmbh, Waldhornlestrasse 17,D72072 Tubingen, Germany.

Figure 9:
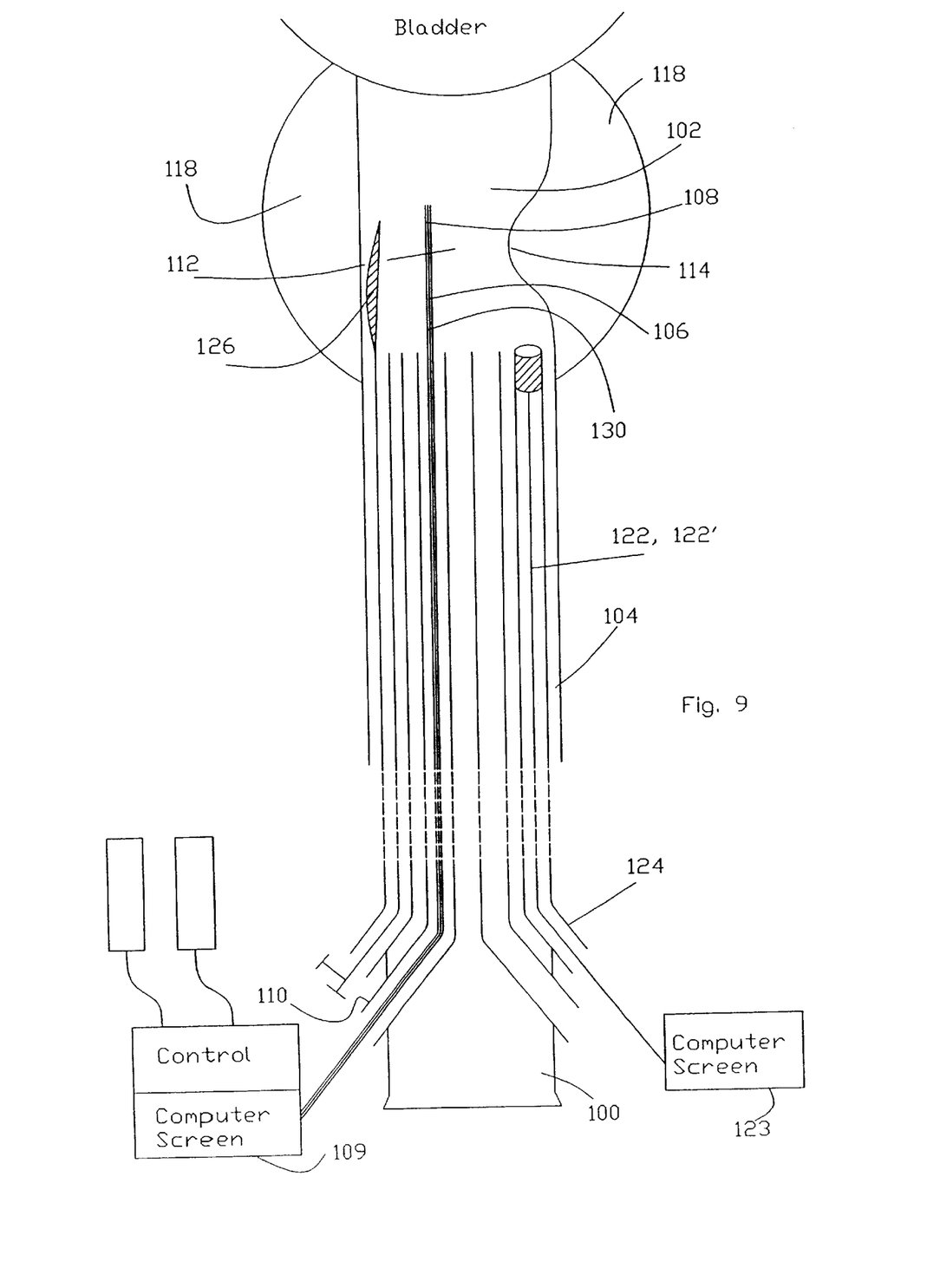
FIGS. 9–10 are schematic cross sectional views demonstrating the use of a probe of a cryoprobe in a cryosurgical procedure according to the method of the present invention.
Figure 10:
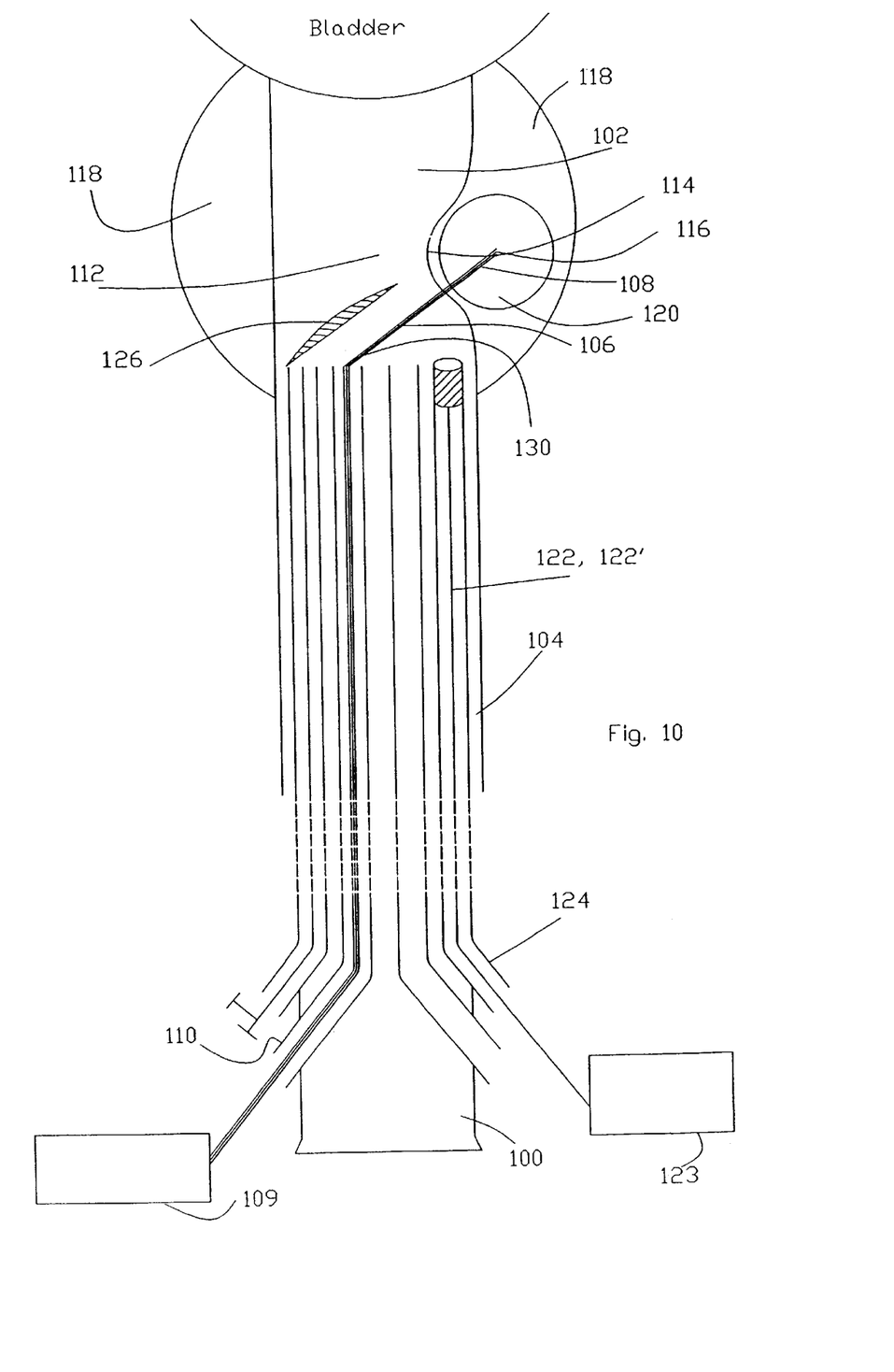

The method according to the present invention is effected by implementing the following method steps which are demonstrated in context of FIGS. 9–10, in which, in a first step a cystoscope 100 is inserted into a prostatic urethra portion 102 of a urethra 104 of a patient having benign prostate hyperplasia. Cystoscopes suitable for insertion into a urethra are distributed, for example, by KARL STORZ Gmbh & Co. Mittelstr. 8, D-78532 Tuttlingen; and Richard Wolf Gmbh, 75434 Knittlingen, Postfach 1164/1165 Germany. Some cystoscopes are provided with built-in video and some without. All cystoscopes are insertable into the urethra. Insertion is preferably executed following administration of local anesthesia, such as lidocaine or esracaine, to reduce uncomfort.

In a second step of the method a probe 106 of a cryoprobe having an operating tip 108 is guided through a channel 110 of cystoscope 100 to a portion, e.g., an obstructed portion, 112 of prostatic urethra 102. The obstructed portion can, for example, be as a result of a benign prostate hyperplasia.

In a third step of the method, operating tip 108 is navigated through a wall 114 of prostatic urethra 102 into at least one location 116, at a time, of a prostate 118 of the patient. Operating tip 108 of probe 106 is preferably formed with a sharp end so as to minimize the wound formed in wall 114 of prostatic urethra 102 when effecting the step of navigating operating tip 108 through wall 114 of the prostatic urethra 102 into a desired location within prostate 118 of the patient.

Finally, the cryoprobe is operated, thereby cooling operating tip 108 of probe 106 and producing an ice-ball 120 of prostate tissue around operating tip 108, so as to locally freeze a portion of prostate 118, yet substantially avoid freezing prostatic urethra 102. It will be appreciated that freezing the prostate tissue causes the volume of the prostate to decrease. In particular, ice-ball 120 which forms around operating tip 108 of probe 106 leads to cell destruction at the frozen site. The dead tissue remains in the body and, overtime, is naturally reabsorbed. However, substantially no or little damage is inflicted upon prostatic urethra 102 so as to minimize discomfort and pain during the healing process following the procedure. It will be appreciated that tip 108 limits the extreme cold zone to a small active area close thereto, since the only significant heat transfer occurs where tip 108 is in direct contact with the tissue. The apparent advantage is that the disease free tissue, located next to the trauma, suffers much less than from surgical abscission, or from system that cannot control the ice ball size and the positioning of its operative tip with precision. According to a preferred embodiment, probe 106 is equipped with a thermocouple which is used to monitor the temperature of operating tip 108. The thermocouple is used in conjunction with a computer control unit that displays the information on a screen both shown at 109. The computer interface serves as mechanism of controlling tip's 108 temperatures and monitoring the performance of probe 106.

This procedure is repeated a required number of times until sufficient cryoablation has been achieved. When sufficient cryoablation has been applied probe 106 is retracted from channel 110 of cystoscope 100. Thereafter, cystoscope 100 is retracted from urethra 104.

According to a preferred embodiment of the present invention inserting cystoscope 100 into prostatic urethra portion 102 of urethra 104 of the patient is aided using an optical probe 122 inserted through an optical channel 124 of cystoscope 100. It will be appreciated that optical probe 122 can be an integral part of cystoscope 100. In other words, cystoscope 100 can include a built-in optical channel 122'. Any suitable optical probe can be employed with cystoscope 100, examples include, but are not limited to, probes distributed by KARL STORZ Gmbh & Co. Mittelstr. 8, D-78532 Tuttlingen; and Richard Wolf Gmbh, 75434 Knittlingen, Postfach 1164/1165 Germany. A computer operated screen 123 communicating with probe 122 or channel 122' serves for viewing. It will be appreciated that computer operated screen 123 can be integrated in computer control unit and screen 109.

According to another preferred embodiment of the present invention navigating operating tip 108 through wall 114 of prostatic urethra 102 into at least one location 116 of prostate 118 of the patient is aided using optical probe 122 or built-in optical channel 122'.

The incorporation of video-assisted cystoscopy allows to continuously monitor the procedure so as to accurately direct operating tip 108 to predetermined sites of the treated tissue and to control the depth of penetration into the tissue.

In addition, or as a sole guiding mechanism ultrasound monitoring externally applied at the lower abdomen region is employed for navigating operating tip 108 through wall 114 of prostatic urethra 102 into at least one location 116 of prostate 118 of the patient. A suitable ultrasound is distributed by B&K MEDICAL, Sandtoften 9, DK 2820 Gentofte, Denmark, DA. The ultrasound not only assists in appropriately locating tip 108 within prostate 118, rather it is used to evaluate the constriction and the required size and number of ice-balls 120 which will effectively remove the constriction of prostatic urethra 102. It is further used to monitor the formation of an ice-ball 120, so as to enable an operator to precisely control the size thereof in real time.

According to yet another preferred embodiment of the method according to the present invention operating tip 108 of probe 106 is heated so as to melt at least an inner portion of ice ball 120 and enable navigating operative tip 108 away from the portion of the prostate that underwent cryoablation. Thus, when ice ball 120 which is formed around tip 108 is of appropriate size, the freeze procedure is turned off and a thaw procedure is turned on. After a few seconds tip 108 can be removed from the tissue.

According to still another preferred embodiment of the present invention cystoscope 100 is supplemented with a navigation mechanism 126 operative therewith. Navigation mechanism 126 serves to effect the step of navigating operating tip 108 through wall 114 of prostatic urethra 102 into a desired location within prostate 118. In the example of FIGS. 9–10 mechanism 126 is realized as a rotatable article hingedly connected at a distal end of cystoscope 100 and rotatable from an upright position shown in FIG. 9 to a bent position shown in FIG. 10 to thereby urge operating tip 108 through wall 114 of prostatic urethra 102 into a desired location within prostate 118. To this end, probe 106 is designed flexible at least at a portion thereof 130 adjacent operating tip 108.

The new era of cryotherapy allows a more controllable and precise treatment, unique in its ability to destroy the entire unwanted tissue, while keeping the surrounding tissue absolutely intact. The surgeon no longer chooses between incomplete elimination of unwanted tissue and compromising nearby organs, since a small cryoprobe can readily create a precise ovoid shaped ice ball of 12 mm×20 mm.

The method according to the present invention provides numerous advantages over existing techniques for treating benign prostate hyperplasia. It offers a minimally invasive procedure, prevents bleeding and obviates the need for general anesthesia, thus allowing the patient to be treated in the urologist's office, it ensured shorter and more pleasant post operation recovery period since no sloughing of tissue is experiences, since monitoring measures are undertaken to prevent substantial urethral tissue damage, therefore no long-term hormone treatments or post treatment catheter are required.

Evidently, implementing the method of the present invention for treating benign prostate hyperplasia prevents or reduces side effects which characterize prior art treatments. For example, heat ablation therapies which burn the treated tissue cause irreversible damage to peripheral tissues due to protein denaturation and destruction of nerves and blood vessels. Furthermore, heat generation causes secretion of substances from the tissue which may endanger the surrounding area.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for treating benign prostate hyperplasia, the method comprising the steps of:
    (a) inserting a cystoscope into a prostatic urethra portion of a urethra of a patient having benign prostate hyperplasia;
    (b) guiding a probe of a cryoprobe having an operating tip through a channel of said cystoscope to a portion of said prostatic urethra;
    (c) navigating said operating tip through a wall of said prostatic urethra into at least one location at a time of a prostate of said patient; and
    (d) operating said cryoprobe thereby cooling said operating tip and producing an ice-ball of prostate tissue around said operating tip, so as to locally freeze a portion of said prostate, yet substantially avoid freezing said prostatic urethra.

2. The method of claim 1, further comprising the step of:
    (e) retracting said probe from said channel of said cystoscope.

3. The method of claim 2, further comprising the step of:
    (f) retracting said cystoscope from said urethra.

4. The method of claim 1, wherein said step of inserting said cystoscope into said prostatic urethra portion of said urethra of said patient having benign prostate hyperplasia is aided using an optical probe inserted through an optical channel of said cystoscope.

5. The method of claim 1, wherein said step of navigating said operating tip through said wall of said prostatic urethra into at least one location at a time of said prostate of said patient is aided using an optical probe inserted through an additional channel of said cystoscope.

6. The method of claim 1, wherein said step of navigating said operating tip through said wall of said prostatic urethra into at least one location at a time of said prostate of said patient is aided using a built-in optical channel of said cystoscope.

7. The method of claim 1, wherein said step of navigating said operating tip through said wall of said prostatic urethra into at least one location at a time of said prostate of said patient is aided using ultrasound monitoring.

8. The method of claim 1, wherein said step of navigating said operating tip through said wall of said prostatic urethra into at least one location at a time of said prostate of said patient is aided using an optical channel of said cystoscope and ultrasound monitoring.

9. The method of claim 1, further comprising the step of:
(e) prior to executing said step of inserting said cystoscope into said prostatic urethra portion of said urethra of said patient having benign prostate hyperplasia, providing said patient with local anesthesia.

10. The method of claim 1, further comprising the step of:
(e) heating said operating tip so as to melt at least an inner portion of said ice ball and navigating said operative away from said portion of said prostate.

11. The method of claim 1, wherein said cystoscope has a navigation mechanism operative therewith, said navigation mechanism serves to effect said step of navigating said operating tip through said wall of said prostatic urethra into at least one location at a time of said prostate of said patient.

12. The method of claim 1, wherein said operating tip of said probe is formed with a sharp end so as to minimize the wound formed in said wall of said prostatic urethra when effecting said step of navigating said operating tip through said wall of said prostatic urethra into at least one location at a time of said prostate of said patient.

13. The method of claim 1, wherein said probe is flexible at least at a portion thereof adjacent said operating tip.

14. The method of claim 1, wherein said probe of said cryoprobe includes a heat exchanger coupled to an orifice, the orifice opening into a jacket; said jacket forming a reservoir capable of housing a fluid in contact with said at least one location, at a time, of said prostate of said patient; said cryoprobe further includes two gas sources providing two gases, each of said two gas sources being independently connected to said heat exchanger of said probe, and a mechanism for allowing and stopping a flow of each of said two gases through said orifice.

15. The method of claim 14, wherein said gas sources are pressurized, pressurized gas sources are gas reservoirs containing gas under pressure.

16. The method of claim 14, wherein said gas sources include one or more compressors, which draw gas from a reservoir containing gas at a lower pressure than desired.

17. The method of claim 14, wherein said heat exchanger is a thin tube or a porous matrix heat exchanger.

18. The method of claim 1, wherein said probe of said cryoprobe includes (i) a heat exchanger coupled to an orifice, the orifice opening into a jacket; and (ii) the jacket which is in contact with the surface to be heated and cooled, the jacket forming a reservoir capable of housing a fluid in contact with a surface to be heated and cooled; said cryoprobe further includes
(a) two independent connections for pressurized gas sources, connected to the heat exchanger;
(b) temperature generation mechanism, coupled to the probe, including:
(i) two independent pressurized gas sources, connected to the probe through the two independent connections;
(ii) controllable gas flow valves to permit or preclude a flow of each of gases from the independent pressurized gas sources into the probe; and
(c) processing mechanism for controlling the controllable gas flow rate valves according to predetermined operating conditions.

19. The method of claim 18, wherein said cryoprobe further includes a data input mechanism, to provide operation data to said processing mechanism.

20. The method of claim 19, wherein said data input mechanism includes a keyboard.

21. The method of claim 20, wherein said cryoprobe further includes display mechanism to display data written to, or read from, said processing mechanism.

22. The method of claim 19, wherein said data input mechanism includes a communication port.

23. The method of claim 22, wherein said communication port is an RS232 port.

24. The method of claim 19, wherein said data input mechanism includes a magnetic or optical reading mechanism, to read pre-prepared data.

25. The method of claim 24, wherein said cryoprobe further includes a temperature-reading mechanism located at or near said operating tip, which temperature-reading mechanism provides temperature readings to said processing mechanism.

26. The method of claim 25, wherein said temperature-reading mechanism includes one or more thermocouples.

27. The method of claim 26, wherein said cryoprobe further includes a pressure-reading mechanism located between the pressurized gas source and said probe, to provide to said processing mechanism readings corresponding to pressure supplied by each of said pressurized gas sources.

* * * * *